United States Patent
Collins et al.

(10) Patent No.: US 7,660,448 B2
(45) Date of Patent: Feb. 9, 2010

(54) AUTOMATED LESION CHARACTERIZATION

(75) Inventors: Michael J. Collins, Beavercreek, OH (US); Daniel Corwin-Renner, Ann Arbor, MI (US)

(73) Assignee: iCAD, Inc., Beavercreek, OH (US)

( * ) Notice: Subject to any disclaimer, the term of this patent is extended or adjusted under 35 U.S.C. 154(b) by 1018 days.

(21) Appl. No.: 10/993,187

(22) Filed: Nov. 19, 2004

(65) Prior Publication Data

US 2005/0111716 A1 May 26, 2005

Related U.S. Application Data

(60) Provisional application No. 60/525,513, filed on Nov. 26, 2003.

(51) Int. Cl.
*G06K 9/00* (2006.01)
(52) U.S. Cl. ......................... 382/128; 382/130; 382/132
(58) Field of Classification Search ................. 382/128, 382/130–133, 190; 378/4, 37
See application file for complete search history.

(56) References Cited

U.S. PATENT DOCUMENTS

| | | | |
|---|---|---|---|
| 6,198,838 B1 | 3/2001 | Roehrig et al. |
| 6,266,435 B1 | 7/2001 | Wang |
| 6,434,262 B2 | 8/2002 | Wang |
| 6,477,262 B2 | 11/2002 | Wang |
| 6,574,357 B2 | 6/2003 | Wang |
| 6,628,815 B2 | 9/2003 | Wang |
| 7,054,473 B1 | 5/2006 | Roehrig et al. |
| 7,203,350 B2 | 4/2007 | Leichter et al. |
| 2002/0097902 A1 | 7/2002 | Roehrig et al. |
| 2006/0122467 A1 | 6/2006 | Harrington et al. |

*Primary Examiner*—Duy M Dang
(74) *Attorney, Agent, or Firm*—Foley Hoag LLP

(57) ABSTRACT

A method and system that provides users with additional information regarding imagery analyzed by computer-aided detection (CAD) systems is described. A user selects a region of the analyzed imagery. Information is then derived from computational measurements of the region obtained during CAD processing. The region selected by the user does not necessarily have to include a displayed CAD system detection. The information includes a description of the computational measurement and the value of the measurement, both of which are provided in clinically relevant terms.

55 Claims, 4 Drawing Sheets

AUTOMATED LESION CHARACTERIZATION

CROSS-REFERENCE TO RELATED APPLICATIONS

This application claims the benefit of U.S. Provisional Application No. 60/525,513, filed Nov. 26, 2003, incorporated herein by reference.

BACKGROUND OF THE INVENTION

1. Field of the Invention

The present invention generally relates to computer-aided detection (CAD) of abnormal regions in medical imagery and, in particular, relates to providing information regarding why a particular region of the imagery was or was not displayed with a corresponding CAD system detection.

2. Discussion of Background

CAD systems are becoming widely used to assist readers of medical imagery. Such systems are commercially available to assist radiologists in the detection of signs of cancer in mammographic and chest imagery by highlighting regions of possible malignancies. In essence, the CAD systems become a second reader of the medical imagery for the radiologist.

At a fundamental level, CAD system operation may be explained as the sequence of operations, comprising, in order, detection, discrimination, and display. In detection, input imagery is analyzed to locate candidate regions with characteristics typical of malignancies. The input imagery can be from a variety of sources including digitized film and systems which directly create digital images. In mammography, separate processing paths are typically provided to individually detect common types of cancer: a mass detector and a clustered microcalcification detector. A set of measurements or features is computed from the candidate regions. The set of features is input to a discrimination process which determines whether to accept or to dismiss each candidate region. In the display step, the collection of candidate regions accepted by the discrimination step is shown to a user, typically a radiologist.

In practice, many users become accustomed to the operation of the CAD system. Most CAD system outputs are readily interpreted by users. That is, a displayed detection is either accepted as malignant or is easily dismissed as a false positive mark due to some observable artifact in the image. However, users may occasionally desire more information about the reasons a region was marked. Additionally, in some cases, it is foreseeable that users may desire more information about regions in an image that are not marked by the CAD system. Since CAD systems typically base display decisions on computed numerical scores from a plurality of measurements, there is no current method for providing feedback to a radiologist regarding why a particular image region was marked or not.

Therefore, there is a need for providing information to users regarding the factors influencing a CAD system's determination about whether or not to mark a particular region as a detection.

SUMMARY OF THE INVENTION

According to the present invention, additional information regarding imagery analyzed by computer-aided detection (CAD) systems is provided and interactively displayed to users. A user selects a region of the analyzed imagery on an output display. Information is then derived from computational measurements of the selected region obtained during CAD processing. The region selected by the user does not necessarily need to include a displayed CAD system detection. The derived information displayed to the user includes both a description of the computational measurement and the value of the measurement, both the value and the description are provided in clinically relevant terms.

Accordingly, it is an object of the present invention to provide information to users regarding the factors influencing a CAD system's determination about whether or not to mark a particular region as a detection on an output display.

Other objects and advantages of the present invention will be apparent in light of the following description of the invention embodied herein.

BRIEF DESCRIPTION OF THE DRAWINGS

The following detailed description of specific embodiments of the present invention can be best understood when read in conjunction with the following drawings, where like structure is indicated with like reference numerals, and in which.

DETAILED DESCRIPTION OF THE PREFERRED EMBODIMENTS

In the following detailed description of the preferred embodiments, reference is made to the accompanying drawings that form a part hereof, and in which are shown by way of illustration, and not by way of limitation, specific preferred embodiments in which the invention may be practiced. It is to be understood that other embodiments may be utilized and that logical, mechanical and electrical changes may be made without departing from the spirit and scope of the present invention.

Figure 1:
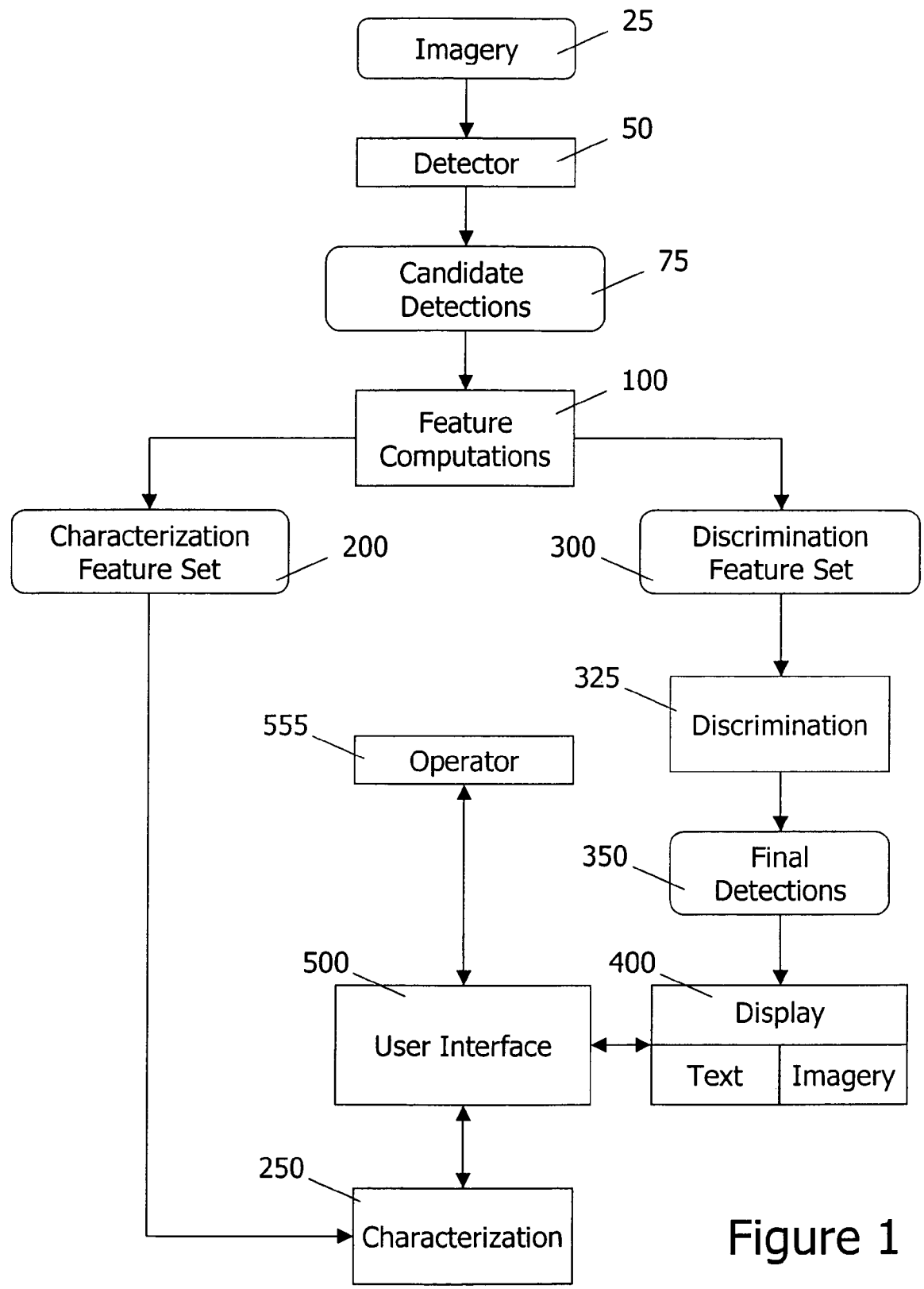
FIG. 1 is an overview of the method for providing automated lesion characterization information to a user according to an embodiment of the present invention.

An overview of the method for providing information to users regarding the factors influencing the CAD system's determination about whether or not to mark a particular region is shown in FIG. 1. Input imagery, 25, is provided to a detector stage, 50. In one embodiment, the detector stage provides locations of a plurality of lesion types, producing candidate regions, 75. Candidate regions therefore consist of lesion location and type. A plurality of features regarding the candidate regions are computed in step 100. A predetermined collection of features is formed in step 300 for subsequent use in discrimination step 325. Candidate regions passing the discrimination step are identified as Final Detection indicators, 350. Final detection indicators are a subset of the original candidate region set, and are displayed on an output device 400, for review by a user, 555. The output device supports display of imagery in an image field and text information in a text field. Final detection indicators are displayed as markers overlaid on the input imagery, with the marker shape indicating the type of lesion.

When the user desires more information about a particular region in the displayed imagery, a point in that region is specified through a user input interface, 500. In one embodiment, the user input interface is a touch screen but other modes of user input interface are possible such as, for example, a keyboard, spaceball or a mouse. Significantly, the selected point does not necessarily need to be located in an image region with a final detection. The set of candidate CAD detections closest to the selected point is located. If the distance between the selected point and the closest CAD detection is less than a predetermined value, information regarding the region is displayed in the text field of the display device 400.

Information regarding the region is obtained from the characterization feature set, 200. The characterization feature set is a predetermined collection of measurements deemed to be associated with visual qualities useful for helping a user determine "Why did this region (not) receive a CAD detection?" Characterization features associated with a selected region are input to a characterization step, 250. Here, feature values are converted to textual information and displayed for the user in the text field of the display device. Most importantly, the characterization information is available for any selected region within a predetermined distance of a candidate detection, regardless of whether or not the candidate detection is displayed at the output of the CAD system. Furthermore, the textual information serves to translate the image processing and computational feature descriptions into terms more applicable to the clinical setting. Also important to note is that the feature information displayed to the user is not necessarily limited to be from the group of features used in the discrimination step, 325.

Detection

In the detector step, 50, candidate regions are generated from image areas with characteristics typical of malignancies. Typically, separate processing paths are provided to individually detect common types or indicators of cancer. In mammography, for example, separate detectors for locating candidate masses, spiculated masses, and clusters of microcalcifications are known in the art. A collection of candidate regions, 75, is created from the input imagery. Candidate regions include information regarding the type of lesion and its location. Lesion type information is obtained by recording which detector produced the candidate region.

It is possible for more than one detector to indicate the same region of an image. CAD systems typically use domain specific knowledge to determine how to assign detection marks in such situations. For example, in mammography, it is reasonable to allow mass and microcalcification detections to indicate the same region of an image.

Discrimination

In step 100, a set of features is computed from image regions associated with the candidate regions. A subset of these features are identified as relevant for discrimination and associated with the Discrimination Feature Set, 300, for input to a discrimination step, 325. Discrimination can be accomplished by means known in the art, see for example, Bishop's *Neural Networks for Pattern Recognition* (Oxford University Press, 1995), Fukunaga's *Introduction to Statistical Pattern Recognition* (Academic Press, NY, 1990), and Duda, Hart and Stork's *Pattern Classification* ($2^{nd}$ Edition, JW Wiley and Sons, NY, 2000). The objective of discrimination is to separate the candidate regions into two classes: a first class of regions to display as CAD system final detections on output imagery, 350, and a second class of regions not to be displayed as CAD system detections.

Display

Figure 2:
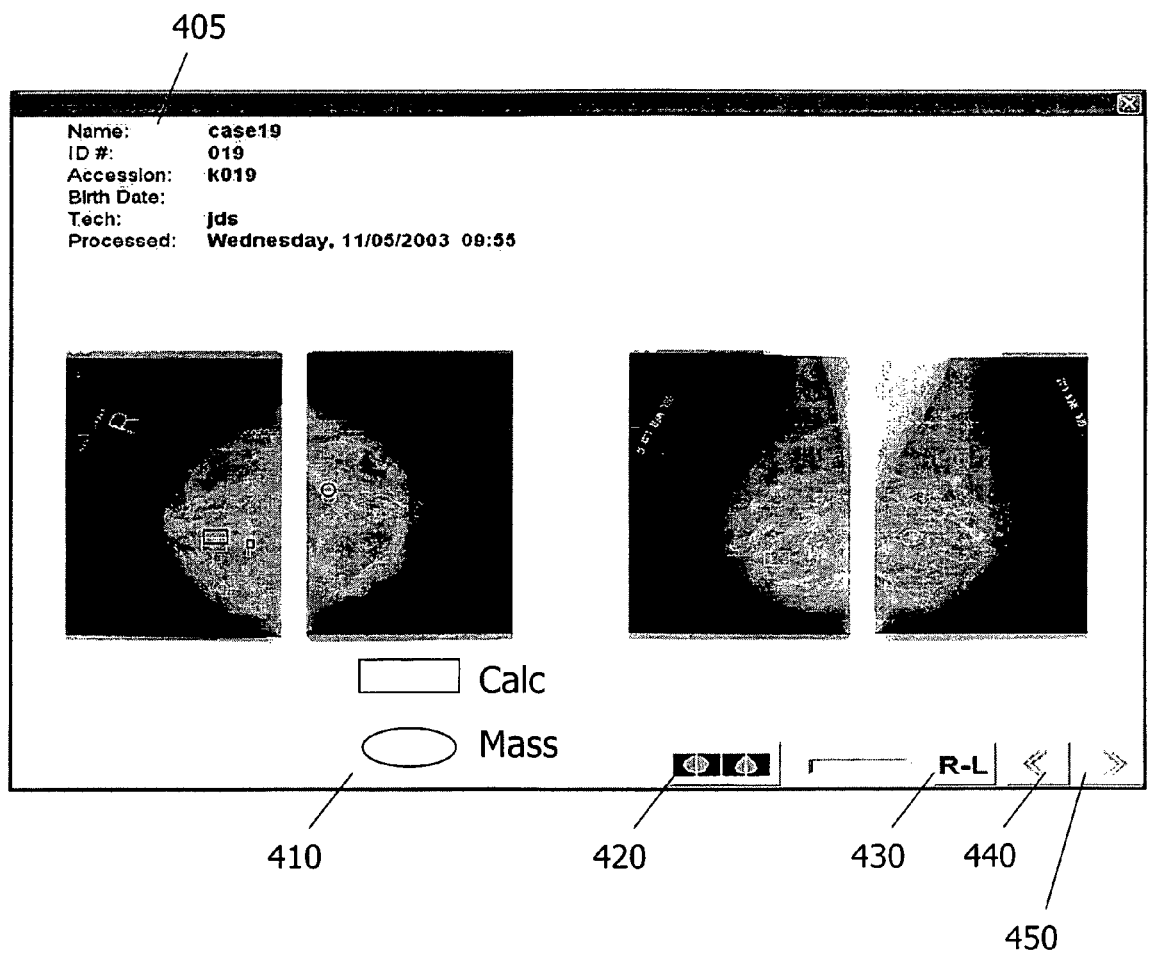
FIG. 2 is an example of the system display in the Normal Mode according to an embodiment of the present invention.

In the display step, 400, the collection of candidate regions accepted by the discrimination step is shown to a user via an output device. The output device can be any type of monitor or display, such as, for example, a computer monitor, LCD flat screen, a CRT monitor, a plasma screen or any other similar device. As indicated in FIG. 1, the display step supports allocation of portions of the display to text and imagery. CAD detections are typically displayed overlaid on the imaged body part in an image field of the display along with patient information in a text field of the display, as shown in FIG. 2, an example CAD system output. In this mammography example, suspicious clusters of microcalcifications are indicated with rectangles and suspicious masses are indicated with ellipses, as indicated by the legend, 410.

User Interface

A primary function of the user interface is to control the display mode. In one embodiment, the user interface is a touch screen monitor that also serves as the output device. Other modes of user interface are possible and may include, for example, a keyboard or a mouse. Three display modes are provided, comprising Normal, Zoom, and Characterization. In the Normal display mode, the images of the case are displayed with fewer pixels than the native digital images. The button 420 causes the display to be shown in the Normal mode. The button at 430 changes the ordering of the images in the display. For example, these images are ordered from left to right as Right cranio-caudal (CC), Left CC, Right mediolateral oblique (MLO), and Left MLO. In one embodiment, clicking button 430 changes the ordering to Left CC, Right CC, Left MLO, and Right MLO. Other orderings may be specified by individual users. Button 440 causes the prior case in a queue of cases under review to be displayed while button 450 causes the next case in the cue to be displayed.

Figure 3:
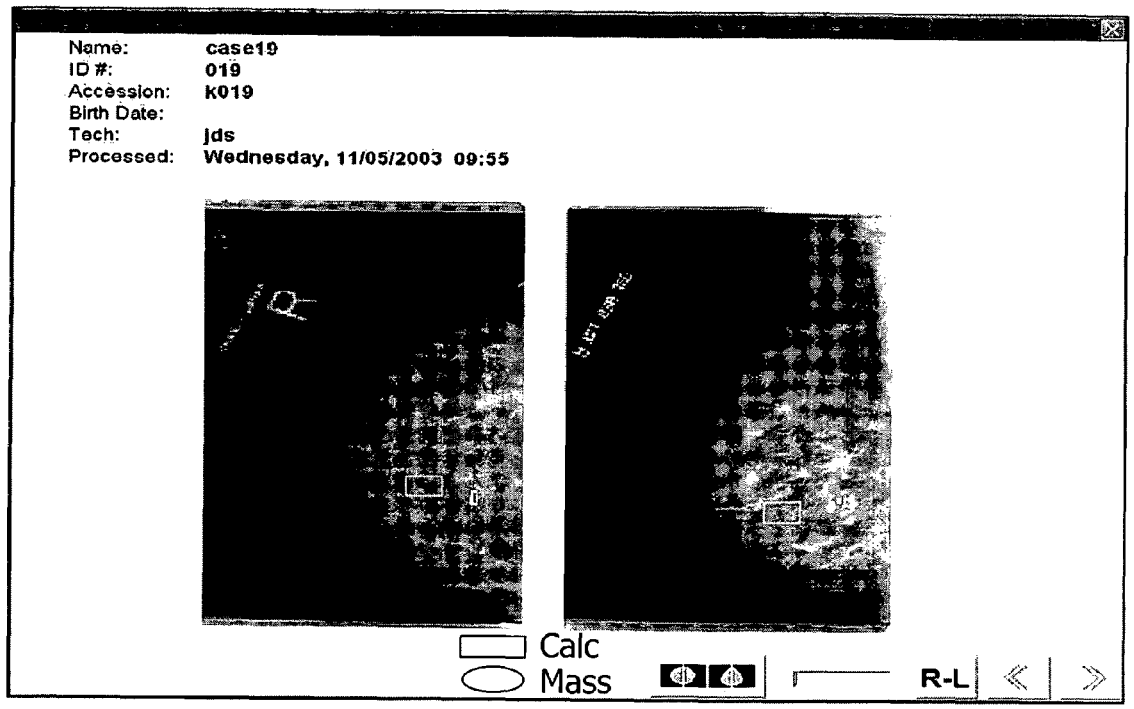
FIG. 3 is an example of the system display in the Zoom Mode according to an embodiment of the present invention.

To receive characterization information about a particular region, a user first chooses a particular image from an image displayed in the normal low resolution mode. In one embodiment, choosing an image is accomplished by touching the desired image of the normal display mode. Other modes of choosing an image are also possible, such as, for example, a mouse or a keyboard. If an image is chosen while the display is in the Normal Mode, the display changes to the Zoom mode, as shown in FIG. 3.

In Zoom mode, higher resolution images of both views of the selected breast are displayed. When the display operates in the Zoom mode, the user has the capability to interrogate specific regions of the displayed images. In one embodiment, interrogation of a specific region is supported by a user using a touch screen. Other modes of user interface are possible, such as, for example, through the use of a keyboard or a mouse. The user may interrogate regions with or without displayed CAD detections.

Figure 4:
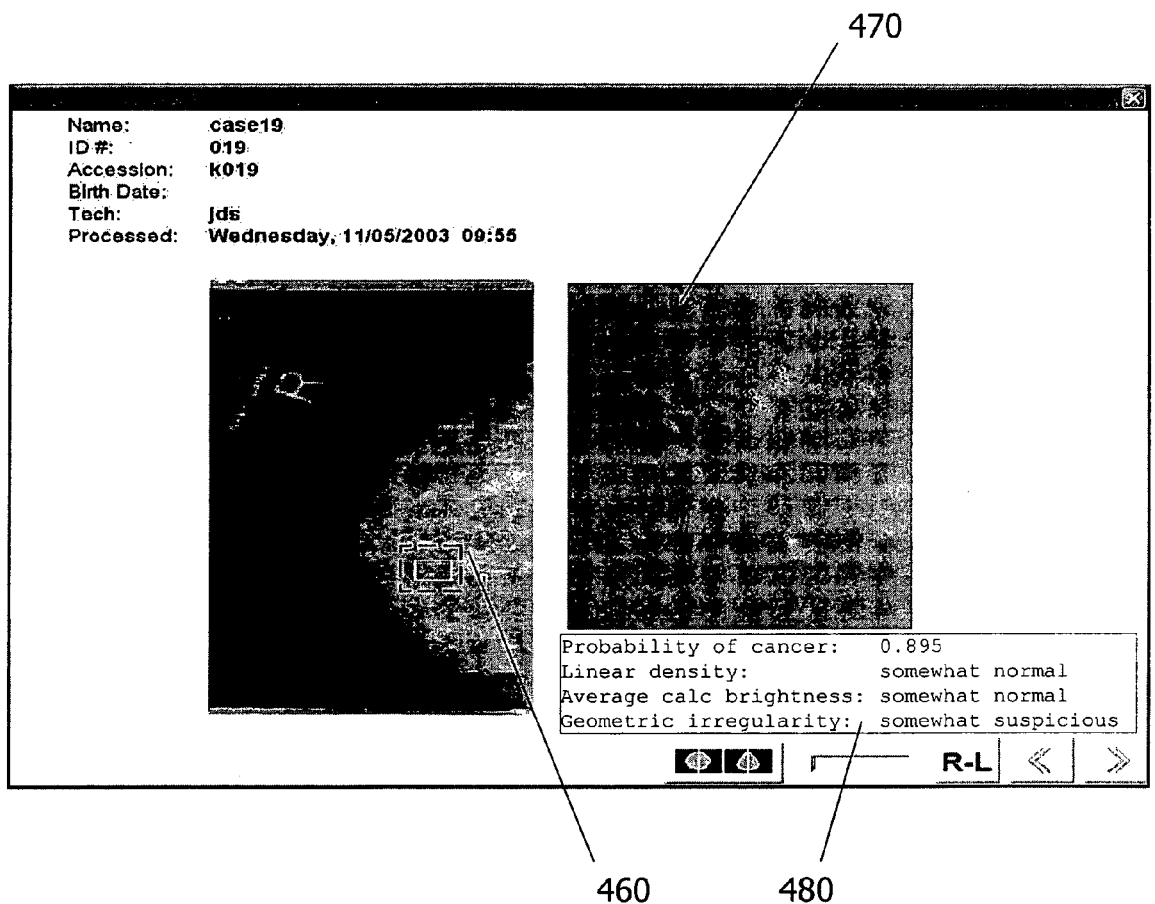
FIG. 4 is an example of the system display in the Characterization Mode according to an embodiment of the present invention.

When a user touches, or selects, any point within a displayed CAD detection, the display changes to the Characterization Mode, as shown in FIG. 4. In this case, a zoom characterization marker, 460, is automatically defined to include an area including the detection. As high a resolution as possible version of the image within the characterization marker is displayed on the right half of the display, as seen in 470. Characterization information is provided textually in the characterization window, 480. A user may also interrogate a portion of an image without a displayed CAD detection. In one embodiment, the user selects a location on an image to interrogate. A high resolution version of the image neighborhood about the selected location is displayed in the right half of the display. The subimage area shown in the high resolution display depends on whether or not an initial CAD detection exists in the neighborhood of the selected location. If an initial CAD detection exists in the neighborhood of that point, the area is determined as in the situation of an existing displayed CAD detection. If no CAD detection exists in the neighborhood of the selected point, a predetermined area is displayed and the user is informed that no CAD detections exist in that area. In an alternative embodiment, the user selects a subimage by dragging a selection tool across an area of the zoomed image. When the region contains an initial or final CAD detection, it is highlighted according to its type in the high resolution image, 470. In another embodiment, detected densities are outlined and microcalcifications are indicated by arrows. The example shown in FIG. 4 highlights individual microcalcifications.

In an alternative embodiment of the invention, users are permitted to skip the Zoom mode. In this embodiment, users simply indicate an image location from the Normal mode display of FIG. 2, then the display changes directly to the Characterization mode as in FIG. 4. Users can specify their preference to work in this embodiment by a predetermined configuration file or by providing an input with the user interface.

Characterization

In the Characterization step, 250, of FIG. 1 information is displayed for image regions selected by the user. Information includes a probability of cancer for the region and descriptions regarding the degree of suspiciousness for certain region features. The features used for characterizing a region are obtained from the Characterization Feature Set, and are not limited to those used for discrimination. In one embodiment of the present invention, features are identified and categorized by text descriptions, as seen in 480 of FIG. 4.

Individual features from a detected region are analyzed to determine a score related to that feature's diagnostic relevance for the region. A score is computed from each feature in the Characterization Feature Set, and when the score is in a predetermined informative range, appropriate information is displayed regarding that feature. The scores are computed as follows.

In a training phase, the detector from a CAD system processes a database of truthed imagery, and predetermined characterization features computed for each detected region. The distributions of feature measurements for detections of malignancies, a true positive (TP), and detections of normal tissue, a false positive (FP), are approximated with Gaussian probability density functions (pdf). First, conditional probabilities of the feature given TP and FP detections are computed according to:

$$P_{TP}(x) = \frac{1}{\sigma_{TP}\sqrt{2\pi}} \exp\left(-\frac{(x-\mu_{TP})^2}{2\sigma_{TP}^2}\right) \quad (1)$$

$$P_{FP}(x) = \frac{1}{\sigma_{FP}\sqrt{2\pi}} \exp\left(-\frac{(x-\mu_{FP})^2}{2\sigma_{FP}^2}\right) \quad (2)$$

where $\mu_{TP}$, $\mu_{FP}$, $\sigma_{TP}$, and $\sigma_{FP}$ are the means and standard deviations of the feature x for detections associated with cancer and normal regions, respectively. Some features may require a power transform to improve the fit of the Gaussian pdf. Power transformation is well known in the art and is described in Fukunaga—Introduction to Statistical Pattern Recognition, 2nd ed., Academic Press, 1990.

The score is then calculated as:

$$\text{Score}(x) = \frac{P_{TP}(x)}{P_{TP}(x) + P_{FP}(x)} \quad (3)$$

Based on the computed score for each of the features from the detection associated with the region, a text label is assigned to the detection. For example, the score ranges and text labels for one embodiment of the present invention are shown in Table 1. Of course, the score ranges and text labels used to categorize the regions may be modified to suit user preferences.

TABLE 1

Conversion of numerical scores to text labels.

| Score | Text Label |
|---|---|
| 0.0-0.2 | "Very normal" |
| 0.2-0.4 | "Somewhat normal" |
| 0.4-0.6 | "Inconclusive" or an empty label |
| 0.6-0.8 | "Somewhat suspicious" |
| 0.8-1.0 | "Very suspicious" |

The American College of Radiology's Breast Imaging Reporting and Data System (BI-RADS®) defines a structure for describing mammographic findings. The structure consists of a set of lesion properties and associated modifiers for the properties. The two primary mammographic indicators of cancer are masses and clusters of microcalcifications. Masses are described with the shape, margin, and density modifiers shown in Table 2. Clusters of microcalcifications are described with the calcification and distribution modifiers shown in Table 3.

TABLE 2

Mass Characterization

| Shape | Margin | Density |
|---|---|---|
| Round | Circumscribed | High |
| Oval | Microlobulated | Equal (isodense) |
| Lobular | Obscured | Low (lower attenuation, but not fat-containing) |
| Irregular | Indistinct | Fat-containing |
| Not applicable | Spiculated | |
| | Not applicable | |

TABLE 3

Microcalcification Characterization

| Calcification | Distribution |
|---|---|
| Round | Grouped or Clustered |
| Punctate | Linear |
| Amorphous | Segmental |
| Pleomorphic | Regional |
| Fine linear | Diffuse or Scattered |
| Fine linear branching | |

Computational characterization using the descriptions of Tables 2 and 3 is accomplished by applying classification rules to characterization features computed from a detected region. The classification rule assigns a modifier for each appropriate property of the detection. That is, detections from the mass detector receive computed shape, margin, and density modifier labels. Methods for designing classification rules are known in the art. In general, decision rules are designed using a training database of hand-labeled lesion properties and associated modifiers.

In practice, when a user clicks a spot on the zoomed image, a check is made to determine if a CAD detection, displayed or not, is within a reasonable distance of that spot. In one embodiment, the reasonable distance is in the interval of 0 to 2 cm. When the CAD detection is within the reasonable distance, scores for each feature are computed. Text descriptions of features with scores less than a lower value or greater than an upper value are displayed along with corresponding text categorizations. Since the purpose of the method is to provide relevant information to a user regarding reasons a particular region was or was not marked by the CAD system, features receiving inconclusive scores are not displayed.

It is possible or a plurality of CAD detections to be within the predetermined reasonable distance. In this situation, the distance from the indicated spot to the centroid of each CAD detection is computed. The detection with the centroid closest to the indicated spot will be displayed in full resolution along with corresponding feature descriptions.

It is also possible for no CAD detections to be within a reasonable distance. In this case, the area around the indicated spot is displayed in the full resolution window centered at the location of the indicated spot, but no feature information is displayed to the user. In one embodiment, a message is provided to inform the user when there is not a CAD detection within the reasonable distance.

System Example

In the present invention, three display modes are provided: Normal, Zoom, and Characterization. An example of system operation is shown in beginning in FIG. 2 with the normal mode where CAD system output images are displayed on an electronic monitor. In the normal mode, the CAD output is displayed on essentially the entire viewable area of the monitor. A typical mammography exam consists of four images, two views of each breast as shown in the figure. From the left to right of the display, the images are CC views of the right and left breasts followed by MLO views of the right and left breasts. CAD system detections are shown as white rectangles for clusters of microcalcifications and white ellipses for masses. Information related to the case is provided at 405 of the CAD system output. In the area marked as 410, the legend designating CAD system outputs as rectangles for microcalcifications and ellipses for masses is provided. The button 420 causes the display to return the Normal mode if the display mode is Zoom or Characterization. The button at 430 toggles the ordering of the images in the display. For example, clicking button 430 will change the order of images to become Left CC, Right CC, Left MLO, and Right MLO. Button 440 causes the prior case in a queue of cases to be displayed while button 450 causes the next case in a queue of cases to be displayed.

When a user selects an image while the display is in the Normal Mode, the display mode switches to the Zoom Mode, where both views of the selected image are displayed as shown in FIG. 3. In Zoom Mode, both views of the breast are displayed on essentially the entire viewable area of the monitor.

When the user indicates a region within an image while the display is in the Zoom Mode, the display mode switches to the Characterization Mode as shown in FIG. 4. In the Characterization Mode, information related to the indicated region is displayed to the user. In this example, the user has selected a region with a displayed detection of clustered microcalcifications a indicated by the dashed rectangle in the left side of the display. The full resolution image chip is shown on the right half of the display. CAD detections are highlighted in the full resolution image in the right half of the display. Individual microcalcification detections are indicated with small arrows.

A textual description regarding measurements corresponding to the selected region is provided in the characterization window, 480. In this example, the overall probability of malignancy is displayed in the first line of the text window. The probability of malignancy is typically computed by the CAD system using the discrimination feature set obtained from the selected region. The characterization window also provides definitions and descriptions of the features from the characterization feature set using text.

Information regarding each feature of the characterization set with scores outside the inconclusive range is presented in terms relevant to clinical practice. For example, the mathematical definition of a characterization feature may be "the compactness of the convex hull of the centroids of the microcalcifications in a cluster." The corresponding definition of such a feature becomes "Geometric irregularity" as shown in 480 of FIG. 4. Furthermore, assuming the score computed for this feature from the selected detection is 0.73, the displayed description is "somewhat suspicious." In one embodiment, the description strings are definable by the user.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

In other words, although the present invention has been described in terms of mammography, those skilled in the art will recognize the applicability to other forms of imagery, including, for example, any data for which imagery is analyzed for regions of interest with computers and subsequently viewed by a user.

We claim:

1. A method for providing characterization information for a region within medical imagery comprising imagery of at least a portion of a human body, analyzed by a suitably programmed computer-aided detection system comprising at least one input device, at least one processor and at least one output device, comprising the steps:

by means of a processor, processing at least a portion of the medical imagery with the computer-aided detection system to detect candidate regions;

by means of a processor, computing discrimination and characterization features for each candidate region;

by means of a processor, separating said candidate regions in a discrimination step into candidate regions accepted for display and candidate regions not to display;

by means of an output device, displaying computer-aided detection system detection indicators at locations corresponding to the accepted candidate regions overlaid on at least a portion of the medical imagery;

by means of an input device, accepting user input to identify a location on the displayed medical imagery;

by means of a processor, computing a characterization score for each characterization feature for candidate detections within a predetermined distance of the identified location; and by means of an output device, displaying in association with at least a portion of the medical imagery a predetermined definition of each characterization feature and the computed characterization score associated with said candidate detections.

2. The method of claim 1, wherein said candidate regions are image regions with characteristics typical of malignancies.

3. The method of claim 1, wherein said candidate regions include information regarding the types of lesions detected by different types of detectors and the locations of said lesions.

4. The method of claim 3, wherein said types of lesions and their locations is obtained by recording said detector type that produced said candidate region.

5. The method of claim 1, wherein separating said candidate regions further comprises using discrimination features.

6. The method of claim 1, wherein displaying said computer-aided detection system indicators further comprises allocating portions of the display to text and to at least a portion of said imagery.

7. The method of claim 1, wherein said computer-aided detection system indicator are displayed as markers which indicate the type of lesion detected by said computer-aided detection system.

8. The method of claim 1, wherein displaying said computer-aided detection system indicators further comprises displaying at least a portion of said imagery and said computer-aided detection system indicators in Normal mode.

9. The method of claim 8, wherein said Normal mode involves displaying at least a portion of said imagery with fewer pixels than in the native digital images.

10. The method of claim 1, wherein displaying said computer-aided detection system indicators involves displaying at least a portion of said imagery in a predetermined order.

11. The method of claim 10, wherein said predetermined order is modified after receiving input from said user.

12. The method of claim 1, wherein accepting user input changes display mode to Characterization mode.

13. The method of claim 1, wherein accepting user input changes display mode to Zoom mode.

14. The method of claim 13, wherein said Zoom mode displays at least a portion of said imagery in higher resolution than said Normal mode.

15. The method of claim 13, wherein accepting user input changes display mode to Characterization mode.

16. The method of claim 13, wherein said Characterization mode displays both at least a portion of said imagery and a textual characterization window.

17. The method of claim 16, wherein said textual characterization window displays textual description regarding measurements as well as definitions and descriptions of said characterization feature.

18. The method of claim 16, wherein said candidate regions in at least a portion of said imagery in said Characterization mode are indicated by outlines and arrows.

19. The method of claim 16, wherein at least a portion of said imagery in said Characterization mode contains highlighted candidate regions.

20. The method of claim 1, wherein accepting user input changes display mode to a user specified mode.

21. The method of claim 1, wherein accepting user input changes display mode to a mode specified in a predetermined configuration file.

22. The method of claim 1, wherein said user input is accepted from one of a touch screen, a keyboard, a mouse, a spaceball, or combinations thereof.

23. The method of claim 1, wherein said location identified by said user input is in a region of said imagery not displaying a computer-aided detection system detection indicator.

24. The method of claim 1, wherein displaying said predetermined definition of each characterization feature information further comprises displaying only candidate detections with computed characterization scores within a predetermined range.

25. The method of claim 24, wherein said predetermined range of scores is from about 0 to about 0.4 and from about 0.6 to about 1.0.

26. The method of claim 1, wherein said output device for displaying said predetermined definition of each characterization feature and the computed characterization score comprises one of a computer monitor, a LCD flat screen, a CRT monitor, a plasma screen or combinations thereof.

27. The method of claim 1, wherein said predetermined distance ranges between about 0 cm to about 2 cm.

28. The method of claim 1, wherein said characterization score for said characterization feature is not displayed when the distance between a candidate detection and said identified location is greater than said predetermined distance.

29. The method of claim 1, wherein said characterization features that have a plurality of characteristic scores within said predetermined distance range further comprises computing a distance from said identified location to a centroid of said candidate region and displaying said candidate region closest to said identified location with said characteristic score.

30. The method of claim 1, wherein said characterization feature information includes textual information.

31. The method of claim 30, wherein said textual information is displayed in clinically relevant terms.

32. The method of claim 30, wherein textual information is defined by said user.

33. The method of claim 1, wherein said computed characterization score is displayed as a textual label.

34. The method of claim 33, wherein said textual label comprises of more than one level of suspicion.

35. The method of claim 33, wherein said textual label comprises of a characterization description which is based on the value of said computed characterization score.

36. The method of claim 35, wherein said characterization description comprises one of very normal, somewhat normal, inconclusive, somewhat suspicious, or very suspicious or combinations thereof.

37. The method of claim 36, wherein an empty textual field is displayed if said characterization description is based on the value of said computed characterization score corresponding to inconclusive.

38. The method of claim 35, wherein said textual label is defined by said user.

39. The method of claim 35, wherein said characterization score for said characterization feature outside said predetermined distance ranges is not displayed and said textual label indicates that there are no candidate detections within said predetermined distance.

40. The method of claim 1, wherein said characterization score is computed by using a conditional probability given a true positive and a conditional probability given a false positive.

41. The method of claim 40, wherein said conditional probabilities are approximated with Gaussian probability density functions.

42. The method of claim 41, wherein a power transform is used to improve the fit of said Gaussian probability density functions.

43. The method of claim 40, wherein said conditional probability of a feature given a true positive is calculated by the equation, $$P_{TP}(x) = \frac{1}{\sigma_{TP}\sqrt{2\pi}} \exp\left(-\frac{(x-\mu_{TP})^2}{2\sigma_{TP}^2}\right),$$

wherein $\mu_{TP}$ and $\sigma_{TP}$ are the means and standard deviations of said feature x computed from data associated with cancer regions.

44. The method of claim 40, wherein said conditional probability of a feature given a false positive is calculated by the equation, $$P_{FP}(x) = \frac{1}{\sigma_{FP}\sqrt{2\pi}} \exp\left(-\frac{(x-\mu_{FP})^2}{2\sigma_{FP}^2}\right),$$

wherein $\mu_{FP}$ and $\sigma_{FP}$ are the means and standard deviations of said feature x computed from data associated with normal regions.

45. The method of claim 40, wherein said characterization score is computed by dividing said conditional probability of a true positive by the sum of said conditional probability of a true positive and said conditional probability of a false positive.

46. The method of claim 1, wherein said characterization feature is one of a predetermined collection of measurements associated with the visual qualities of said imagery.

47. The method of claim 1, wherein the predetermined distance is 0.

48. A method for providing characterization information for a region within medical imagery comprising imagery of at least a portion of a human body, analyzed by a suitably programmed computer-aided detection system comprising at least one input device, at least one processor and at least one output device, comprising the steps:
by means of a processor, processing at least a portion of the medical imagery with the computer-aided detection system to detect candidate regions;
by means of a processor, computing discrimination and characterization features for each candidate region;
by means of a processor, separating said candidate regions in a discrimination step into candidate regions accepted for display and candidate regions not accepted for display;
by means of an output device, displaying at least a portion of said computer-aided detection system processed medical imagery;
by means of an input device, accepting user input to identify a location on said displayed computer-aided detection system processed medical imagery;
by means of a processor, computing a characterization score for each characterization feature for candidate detections within a predetermined distance of said identified location;
by means of an output device, displaying at least a portion of said computer-aided detection system processed medical imagery of said identified location; and
by means of an output device, displaying in association with at least a portion of the computer-aided detection system processed medical imagery a predetermined textual definition of each characterization feature and the computed characterization score associated with said candidate detections only if said characterization feature and said computed characterization score exist within said predetermined distance of said identified location.

49. The method of claim 48, wherein separating said candidate regions further comprises using discrimination features.

50. The method of claim 48, wherein the predetermined distance is 0.

51. A method for providing characterization information for a region within mammographic imagery comprising imagery of at least a portion of a human body, analyzed by a suitably programmed computer-aided detection system comprising at least one input device, at least one processor and at least one output device, comprising the steps:
by means of a processor, processing at least a portion of said mammographic imagery with the computer-aided detection system to detect malignancy candidate regions;
by means of a processor, computing discrimination and characterization features for each malignancy candidate region;
by means of a processor, separating said malignancy candidate regions in a discrimination step into accepted candidate regions to display and candidate regions not to display;
by means of an output device, displaying computer-aided detection system detection indicators at locations corresponding to the accepted malignancy candidate regions overlaid on at least a portion of the imagery;
by means of an input device, accepting user input to identify a location on the displayed imagery;
by means of a processor, computing a characterization score for each characterization feature for candidate detections within a predetermined distance of the identified location; and
by means of an output device, displaying in association with at least a portion of the imagery a predetermined definition of each characterization feature and the computed characterization score associated with said candidate detections.

52. The method of claim 51, wherein separating said malignancy candidate regions further comprises using discrimination features.

53. The method of claim 51, wherein the predetermined distance is 0.

54. A system for providing characterization information for a region within imagery analyzed by a computer-aided detection system, the system comprising:
a computer-aided detection system to detect candidate regions from said imagery;
an input device for accepting user input to identify a location on said imagery;

a processor for computing discrimination and characterization features for each candidate region, for deciding whether to accept the candidate regions in a discrimination step, and for computing a characterization score for each characterization feature for candidate detections within a predetermined distance of the identified location; and an output device for displaying computer-aided detection system detection indicators at locations corresponding to the accepted candidate regions overlaid on the imagery and for displaying a predetermined definition of each characterization feature and the computed characterization score.

55. The system of claim 54, wherein the predetermined distance is 0.

* * * * *